United States Patent [19]

Milius et al.

[11] Patent Number: 4,826,672

[45] Date of Patent: May 2, 1989

[54] ASTATINATED ORGANIC COMPOUNDS

[75] Inventors: Richard A. Milius, Boston, Mass.; Richard M. Lambrecht, Quogue, N.Y.; William D. Bloomer, Wilton, Conn.

[73] Assignee: President and Fellows of Harvard College, Cambridge, Mass.

[21] Appl. No.: 742,206

[22] Filed: Jun. 7, 1985

[51] Int. Cl.[4] .................. A61K 43/00; C07B 39/00
[52] U.S. Cl. ......................... 424/1.1; 534/10; 564/324; 548/575; 570/181; 570/182; 556/87
[58] Field of Search ............................ 424/1.1; 534/10

[56] References Cited

U.S. PATENT DOCUMENTS 4,311,688  1/1982  Burchiel et al. ................... 424/1

OTHER PUBLICATIONS

W. D. Bloomer et al., *Int. J. Radiation Oncology Biol. Phys.*, vol. 10, pp. 341–348, 1984.
W. D. Bloomer et al., *Science*, vol. 212, p. 340, Apr. 1981.
Lavrukhina et al., "Analytical Chemistry of Technetium, Promethium, Astatine and Francium", Ann Arbor, Humphrey, *Science*, 227-260 (1970).
Liu et al., "Halogen Exchanges Using Crown Ethers:—", Int. J. Appl. Radiat. Isot., vol. 36, No. 7, pp. 561–563, 1985.
Brown, Int. J. Appl. Radiat. Isot., (1982), vol. 33, pp. 75–76.
Visser et al., J. Labelled Compound Radiopharm. (1981), vol. 18, No. 6, pp. 799–808.
Visser et al., Compd Radiopharm. (1980), vol. 17, pp. 657–665.
Visser et al., Int. J. Applied Radiat. Isot. (1982), vol. 33, pp. 389–390.
Visser et al., Radiochem. Radioanal. Lett. (1982), vol. 51, pp. 135–141.
Friedman et al., Int. J. Nuclear Med. Biol. (1977), vol. 4, pp. 219–214.
Brown, Radiochem. Radioanal. Lett. (1982), vol. 53, pp. 343–349.
Shiue et al., (1981), Labeled Compd. Radiopharm. (1981), vol. 18, pp. 1039–1046.
Vasaros et al., Radioanal. Lettr. (1982), vol. 50, pp. 275–281.
Meyer et al., Radiochimica Acta, (1977), vol. 24, pp. 81–85.
Seitz et al., (1981), Syn. Commun., vol. 11, pp. 281–284.
Adam et al., (1983), Chem. Commun., p. 733.
Battacharya, (1981), Indian J. Chem., Sect. A 20A:11-19–1121.
Bloomer et al., Int. J. Radiat. Biol., (1980), vol. 38, p. 197.
Seitz et al., J. Organometallic Chem., (1980), 186:C33.
Adam et al., (1981), Abstracts Papers Am. Chem. Soc., Nuclear 53, 182'nd Am. Chem. Soc. Meeting, Aug. 23-28, 1981, New York, N.Y.

*Primary Examiner*—John F. Terapane
*Assistant Examiner*—Virginia B. Caress

[57] ABSTRACT

Methods and kits for incorporating a radioactive astatine isotope (particularly $^{211}$At) into an organic compound by electrophilic astatodestannylation of organostannanes.

28 Claims, 3 Drawing Sheets

ASTATINATED ORGANIC COMPOUNDS

BACKGROUND OF THE INVENTION

This invention was funded at least in part by a grant from the National Cancer Institute (Grant CA 30043) and from the Department of Energy (Grant DE-AC02-776CH0016). The U.S. Government may have rights in this invention.

This invention relates to astatinated organic compounds and their synthesis.

In various biological and medical applications, it is useful to combine a radioactive entity with a biologically active organic compound. One specific such application is the in vivo destruction of tissue such as tumors or other transformed cells using an organic carrier that selectively delivers a radionuclide to the desired tissue site. A large number of variables are balanced in the selection of the appropriate radionuclide, including the type of radiation it emits, its half-life, its decay products, and the ease and speed of conjugation with the organic entity without loss of the selective delivery function, and without serious risk of in vivo release of the radionuclide from its carrier.

A number of radionuclides have been suggested for selective radiotherapy. One such radionuclide is astatine-211 ($^{211}$At), which has a relatively short half life of about 7.2 and which appears to have suitable decay properties, emitting alpha particles of mean energy 6.8 MeV with a mean range of 60 μm in tissue (Brown, *Int. J. Appl. Radiat. Isot.* (1982) 33:75–76). Such radiation may be superior to beta emissions, and it can selectively destroy cells if the radioactive species is delivered to the region outside the cells, without necessitating localization at the cell nucleus (Bloomer et al., *Int. J. of Radiation Oncology, Biology & Physics* (1984) 10:341–348). FIG. 1 is a diagram of the decay of $^{211}$At Realization of $^{211}$At as an effective therapeutic agent requires development and synthesis of a practical delivery vehicle. Bloomer et al. (1984) cited above discloses a colloid of $^{211}$At tellurium. However, it is generally desirable to link $^{211}$At covalently to the delivery vehicle in order to take advantage of the specificity of various organic molecules such as hormones and antibodies for various types of cells. Formation of such covalent compounds requires a rapid, efficient synthesis. The relatively short half-life of $^{211}$At, the relatively low concentrations of practical $^{211}$At source materials, and the loss of $^{211}$At through competing side reactions are serious problems in developing a suitable synthesis strategy.

Various methods of producing At-organic compounds have been disclosed in the art. Visser et al. *J. Labelled Compound Radiopharm.* (1981) 18:799–808; Visser et al. *Compd Radiopharm.* (1980) 17:657–665 and Brown, *Int. J. Appl. Radio Ist.* (1982) 33:75–76 disclose astatination by electrophilic substitution of an organomercuric compound. Specifically, synthesis of astatopyrimidines and astato-steroids is disclosed.

Visser et al. *Int. J. Applied Radiat. Isot.* (1982) 33:389–390 disclose astatination by electrophilic substitution of thallium.

Visser et al. *Radiochem. Radioanal. Lett.* (1982) 51:135–141; and Friedman et al. *Int. J. Nuclear Med. Biol.* (1977) 4:219–224 disclose decomposition of diazonium salts in the presence of astatide to yield isomers of astatine-substituted benzoic acids. 15 Brown, *Radiochem. Radioanal. Lett.* (1982) 53:343 ∝ 349; Shiue et al. (1981) *Labeled Compd. Radiopharm.* (1981) 18:1039–1046; Vasaros et al. *Radioanal. Lettr.* (1982) 50:275–281 disclose astatination by thermal heterogeneous isotope exchange.

Meyer et al. *Radiochimica Acta* (1977) 24:81–85 disclose that AtCl reactions in benzene derivatives result in substitution of hydrogen or halogen with isomeric distribution products.

Aromatic iodo, bromo, fluoro, and tritio compounds have been synthesized by destannylation of aromatic-tin compounds. Seitz et al. (1981) *Syn. Commun.* 11:281–284; Adam et al. (1983) *Chem. Commun.* p. 733; Battacharya (1981) *Indian J. Chem. Sect. A* 20A:1119-1121; Bloomer et al., *Int. J. Radiat. Biol.* (1980) 38:197; Seitz et al. *J. Organometallic Chem.* (1980) 186:C33; Adam et al. (1981) *Abstracts Papers Am. Chem. Soc.,* Nuclear 53 182'nd Am. Chem. Soc. Meeting, Aug. 23–28, 1981, New York, N.Y.

SUMMARY OF THE INVENTION

The invention features a method of incorporating a radioactive astatine isotope into an organic compound by electrophilic astato destannylation of organostannanes. Specifically, At$^+$ is reacted with the species $R_1$—, $R_2$—, $R_3$—Sn—Z where $R_1$, $R_2$, and $R_3$ are independently selected from aryl and alkyl groups having less than 10 carbons, and Z comprises an unsaturated organic component.

In preferred embodiments, Z is either cell-selective itself (i.e., when exposed to a heterogeneous cell population it binds selectively or is taken up selectively by a subset of the population), or it is chosen to react with a cell selective molecule, such as an antibody or a protein that is specific for a cell-surface receptor. The method can be performed by oxidizing At$^-$ to provide At$^+$, and the reaction can be performed using a kit containing a source of At$^-$ and an oxidizing agent, as well as the organostannane compound described above. Also in preferred embodiments, the reaction is performed in the presence of an electronegative carrier such as Cl$^-$, Br$^-$, or, most preferably, I$^-$. In preferred organostannanes, $R_1$, $R_2$, and $R_3$ are chosen from alkyl groups or substituted alkyl groups of $C_5$ or less, and phenyl or substituted phenyl groups. Z can be a steroidal group, a vinyl group, or an aryl group. The most preferable aryl groups are antibody-coupling aryl groups such as: benzoic acid or a substituted benzoic acid; other carboxylic acids; aromatic amines; aromatic isocyanates; or aromatic isothiocyanates. Z can also be a more complex aryl group such as a vinylestradiol group or tamoxifen group. The preferred At isotope is $^{211}$At.

The electrophilic astato-destannylation reaction enables rapid, efficient production of At-organic compounds such as those suitable for selective, in vivo radiation therapy. In particular, the reaction is useful even at the low concentrations of At (e.g., below 10$^{-6}$M and often below 10$^{-8}$M) present in practical sources of At. The species involved in the reaction exhibit sufficient stability for use in a kit. The reaction is not seriously inhibited by side reactions such as the oxidation of At$^+$ to form relatively unreactive At species. The reaction proceeds under relatively mild conditions using relatively stable reactants that can be stored, and it yields a relatively uncomplicated product mix allowing uncomplicated and rapid isolation. Other features and advantages of the invention will be apparent from the following description of the preferred embodiment and from the claims.

DESCRIPTION OF THE PREFERRED EMBODIMENT

We first briefly describe the figures.

I. Drawings

FIG. 1 is a diagram of the radioactive decay of $^{211}$At

II. Procedure for Manufacture

In preferred embodiments, the electrophilic astatodestannylation is performed by generating $^{211}$At+ through oxidation of $^{211}$At−. One suitable source of Atis Na$^{21}$-1At, but others could be used. First, $^{211}$At is generated on a cyclotron from $^{209}$Bi by the general method described in Bloomer et al. (1984) cited above and in U.S. patent application Ser No. 598,624, filed Apr. 10, 1984 by Lambrecht and Mirzadeh. The isotope is evaporated from the bismuth target material by dry distillation at 650°–680° C., trapped on a column of silica gel and pyrex glass wool and eluted as sodium astatide with a solution of sodium hydroxide (100 mM) an sodium bisulfite (0.1 mM). The 687 and 569 KeV gamma rays from the decay of $^{211}$At and $^{211}$Po can be used for radioassay.

Any of a number of oxidizing agents can be used to oxidize At− to At+. Hydrogen peroxide, periodate, and $I_3{}^-$ are such agents.

Also in preferred embodiments, a carrier species is included to stabilize At− as it is formed to improve the reaction rate and efficiency. While I− (e.g. NaI) is the preferred species, other halides can be used.

Various stannylated organic compounds are known and can be selected to yield the desired astatinated organic compound. The preferred substitution involves a trialkylstannyl (e.g. trimethyl- or tributylstannyl) compounds or triphenylstannyl compounds.

Two specific electrophilic astatodestannylations are described below to illustrate the reaction.

Figure 1:
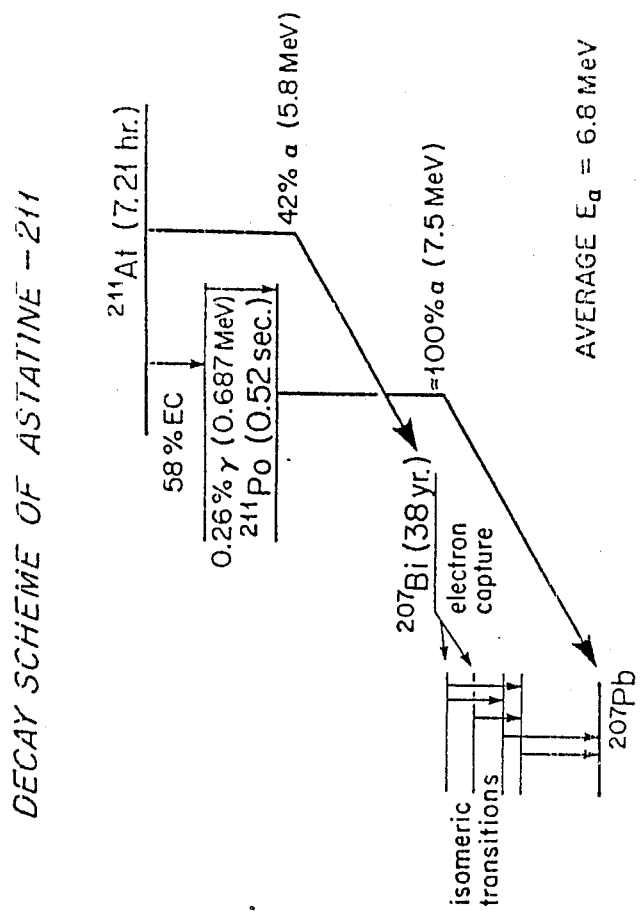
Figure 2:
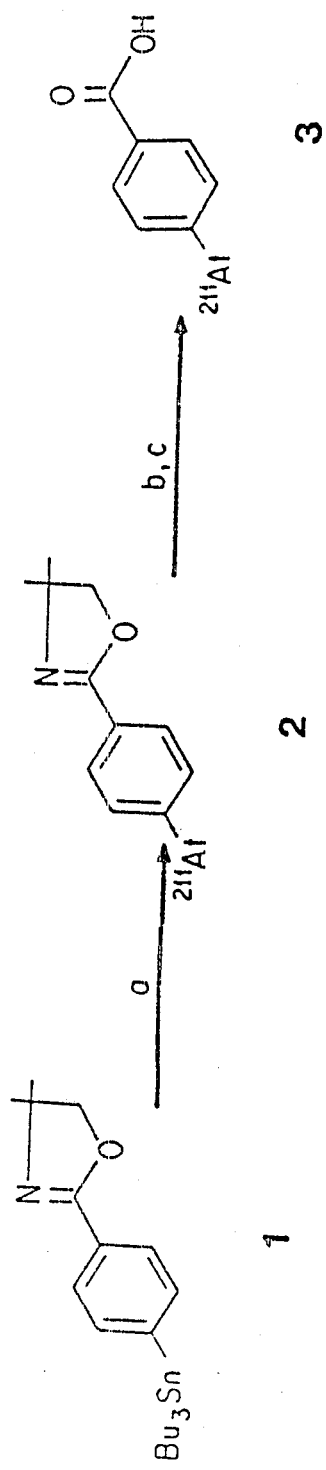
FIG. 2 is a diagram of the formation of $^{211}$At benzoic acid.

A. Synthesis of astatobenzoic acid (FIG. 2).

4-Tri-n-butylstanylbenzoic acid oxazoline (1, FIG. 2) is prepared by the reaction of the lithium aryl derived from 4 bromobenzoic acid oxazoline (t butyllithium, THF, −78° C., 1 min.) with tri-n-butylstannyl chloride, by the method generally described in Meyers et al. *J. Organic Chem.* (1974) 39:2787-2793.

The astatination is performed in a 1 mL conical vial sealed with Teflon septa. Typically, a mixture of 50 μCi of Na $^{211}$At (ca. 10$^{-8}$ μmole), 0.1 mole of sodium iodide and 1.0 μmole of 1 (FlG. 2) in tetrahydrofuran:ammonium acetate buffer, pH 5.0 (50:50, v/v) is treated with 100 μmole of aqueous hydrogen peroxide. After 5 min., the reaction is quenched by the addition of sodium bisulfite. The astatobenzoic acid oxazoline 2 (FIG. 2) could be readily isolated. In practice, however, 4-astatobenzoic acid is generated in situ by brief (10 min.) sequential treatments at 100° C., first with 1N HCl and then with 1N NaOH. Then the mixture is acidified to pH3.

Rapid product isolation is imperative during manipulation of short-lived radionuclides. Accordingly, an expeditious procedure is devised wherein reaction mixtures were passed through a Waters [(Millipore) Milford, Mass.]octadecyl "sep-pak" cartridge. While the organic constituents are thus immobilized, the cartridge is flushed with water to remove unreacted astatide and other inorganic species. Products are recovered by elution of the cartridge with 1–2 mL of either methanol or ethanol, followed by rapid concentration in a stream of nitrogen. Product isolation and identification are achieved by high performance liquid chromatography (HPLC;C 18;EtOH/H$_2$O) or by thin layer chromatography (TLC;silica on plastic;ethyl acetate/hexane or chloroform/methanol). The ultraviolet absorbance of the HPLC eluant is monitored at 280 nm while 0.25 mL fractions are collected for radiometric determination. TLC plates are cut into 3 mm slices to construct the radioactive elution profile.

The product can be characterized and verified by thin layer chromatographic analysis showing co elution of the p-astatobenzoic acid (3 in FIG. 2) with p-iodobenzoic acid. Extraction of an ethyl acetate solution of 3 with 0.1N sodium carbonate efficiently partitions the radioactivity into the aqueous layer; extraction into neutral water or 0.1N hydrochloric acid occurs poorly. The chromatographic behavior of 3 is unaffected by treatment with sodium bisulfite or sodium periodate. The p astatobenzoic acid is stable in hot aqueous acid and base as well as moderately potent reducing and oxidizing agents such as bisulfite, periodate, or peroxide.

Figure 3:
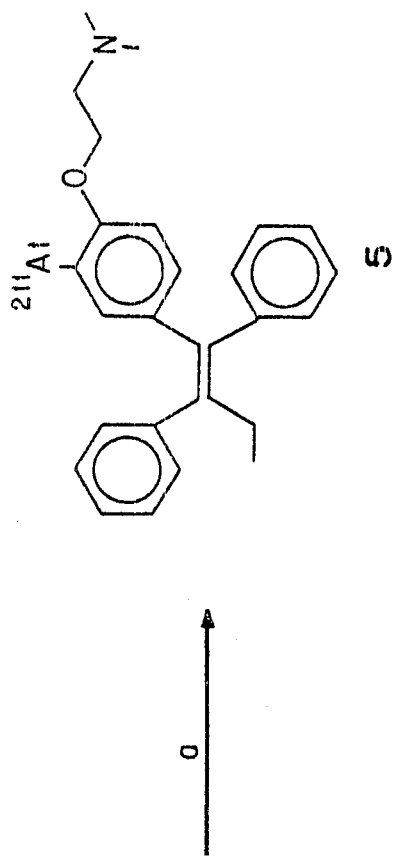
FIG. 3 is a diagram of the formation of $^{211}$At-tamoxifen.
Figure 3:
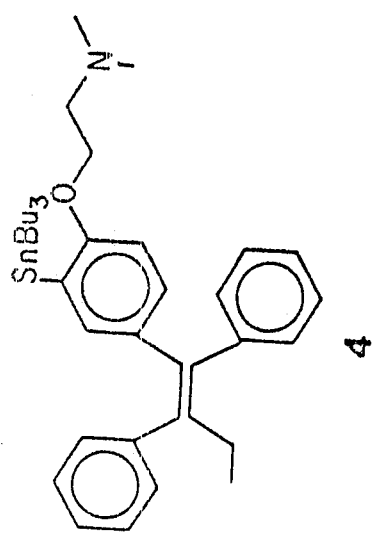

B. Preparation of 3-astatotamoxifen (FIG. 3).

3-Tri-n-butylstannyltamoxifen(4, FIG. 3) is synthesized by the method generally described in Seitz et al. *J. Organomet. Chem.* (1980) 186:C33. The astatodestannylation proceeds as described above for preparation of astatobenzoic acid. 3 astatotamoxifen (5 in FIG. 3) is isolated after HPLC separation. The product can be verified by observing that its radiochromatogram displays a major peak at the same position as 3 iodotamoxifen.

III. Use

The resulting $^{211}$At product can be administered as purified, if the organic entity is a cell selective carrier. Alternatively, if the organic entity is designed to conjugate with a cell-selective carrier, that conjugation is performed prior to administration. For example, p astatobenzoic acid can be conjugated to any of a large number of tumor specific antibodies by the method generally described in Friedman et al. (1977) cited above.

Details of treatment will depend upon the particular tumor cells and cell-specific agents used. Bloomer et al. (1984) cited above provide suitable methods of determining therapeutic efficacy of $^{211}$At agents using animal models. For example, a dosage of 25 μCi provides a surviving cell fraction of 10$^{-6}$ for mouse ascites tumor cells, and the same dosage provides marked attenuation of a mouse tyroid tumor.

Other Embodiments

Other embodiments are within the following claims. For example, other aryl trialkylstannyl starting materials can be used to yield other astatino-aryl compounds. Vinyl-trialkylstannyl compounds can be used to yield astatino-vinyl compounds. The compounds may also be non-cell-selective compounds, e.g. styrenes or styrene polymers that can be formed into a colloidial dispersion and then used as described by Bloomer et al. (1984) cited above or for radiation synovectomy, for example, as a treatment for rheumatoid arthritis as described generally by Sledge et al. Arthritis and Rheumatism 20:1334-1342 (1977).

Kits can be developed composed of separately stored reactants, for example, Na $^{211}$At, an oxidizing agent such as $H_2O_2$, and the stannylated organo compound. Most preferably a source of $I^-$ such as NaI is also included in the kit. If the astatinated organic compound formed is to be conjugated with a cell specific carrier, a source of carrier may also be provided in the kit.

We claim:

1. A method of making the compound At-Z where Z comprises an unsaturated organic component, and At is a radioactive isotope of astatine, said method comprising, providing a source of $At^+$; and reacting said $At^+$ with the compound

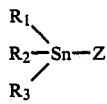

to form At—Z, where $R_1$, $R_2$, and $R_3$, are each independently selected from aryl and alkyl groups having less than 10 carbons.

2. The method of claim 1 wherein Z comprises a cell-specific binding agent or an unsaturated organic linker to a cell specific binding agent.

3. The method of claim 1 wherein said reaction is conducted in the presence of an electronegative carrier.

4. The method of claim 3 wherein said electronegative carrier is $Cl^-$, $Br^-$, or $I^-$.

5. The method of claim 1 wherein said method further comprises generating $At^{30}$ by oxidation of $At^-$.

6. The method of claim 5 wherein said $At^-$ is $^{211}At^-$ supplied in a concentration of less than $10^{-6}M$.

7. The method of claim 1 wherein $R_1$, $R_2$, $R_3$ are each independently selected from alkyl groups or substituted alkyl groups of $C_5$ or less and phenyl or substituted phenyl groups.

8. The method of claim 1 wherein Z is a steroidal group.

9. The method of claim 1 wherein Z is an aryl group, a substituted aryl group, or a vinyl group.

10. The method of claim 9 wherein Z comprises an aryl group capable of coupling with antibodies.

11. The method of claim 10 where Z comprises an aromatic carboxylic acid, an aromatic amine, an aromatic isocyanate, or an aromatic isothio-cyanate.

12. The method of claim 11, wherein Z is a benzoic acid or a substituted benzoic acid group.

13. The method of claim 1 wherein Z is a tamoxifen group or a vinylestradiol group.

14. A kit for performing the method of claim 1 comprising:

a source of $At^-$, an oxidizing agent capable of converting $At^-$ to $At^+$, and a source of said $R_1$—, $R_2$—, $R_3$—Sn—Z.

15. The kit of claim 14 wherein Z comprises a cell-specific binding agent or an unsaturated organic linker to a cell-specific binding agent.

16. The kit of claim 14 wherein said kit further comprises an electronegative carrier species.

17. The kit of claim 16 wherein said carrier is $Cl^-$, $Br^-$, or $I^-$.

18. The kit of claim 14 wherein said At. is $^{211}At^-$ supplied in a concentration of less than $10^{-6}M$.

19. The kit of claim 14 wherein $R_1$, $R_2$, and $R_3$ are each independently selected from alkyl groups or substituted alkyl groups of $C_5$ or less and phenyl or substituted phenyl groups.

20. The kit of claim 14 wherein Z is a steroidal group.

21. The kit of claim 14 wherein Z comprises an aryl group, a substituted aryl group, or a vinyl group.

22. The kit of claim 21 wherein Z comprises an aryl group capable of coupling with antibodies.

23. The kit of claim 22 where Z comprises an aromatic carboxylic acid, an aromatic amine, an aromatic isocyanate, or an aromatic isothio-cyanate.

24. The kit of claim 23 wherein Z is a benzoic acid or a substituted benzoic acid group.

25. The kit of claim 14 wherein Z is a tamoxifen group or a vinylestradiol group.

26. A method of making a cell-selective astatinated compound comprising producting At—Z by the method of claim 2 and reacting At—Z with a cell selective molecule comprising a polypeptide.

27. The method of claim 26 wherein said cell-selective molecule is an antibody or a protein that is specific for a cell surface receptor.

28. A kit for performing the method of claim 26 comprising:

a source of At—Z or materials for making At—Z, and said cell-selective molecule.

UNITED STATES PATENT AND TRADEMARK OFFICE
CERTIFICATE OF CORRECTION

PATENT NO. : 4,826,672
DATED      : May 2, 1989
INVENTOR(S) : Richard A. Milius et al.

It is certified that error appears in the above-identified patent and that said Letters Patent is hereby corrected as shown below:

On the title page, the inventors names should read as follows:

Richard A. Milius, Boston, Mass.;
Richard M. Lambrecht, Quogue, N.Y.;
William D. Bloomer, Wilton, Conn.;
Michael Zalutsky, Chapel Hill, N.C.

Signed and Sealed this

Sixteenth Day of October, 1990

*Attest:*

HARRY F. MANBECK, JR.

*Attesting Officer*   *Commissioner of Patents and Trademarks*